US011407702B2

(12) United States Patent
Tjärnehov et al.

(10) Patent No.: US 11,407,702 B2
(45) Date of Patent: Aug. 9, 2022

(54) METHOD FOR PRODUCING METHANOL IN A REACTOR WITH BYPASS

(71) Applicant: HALDOR TOPSØE A/S, Kgs. Lyngby (DK)

(72) Inventors: Emil Andreas Tjärnehov, Limhamn (SE); Per Juul Dahl, Vedbæk (DK)

(73) Assignee: HALDOR TOPSØE A/S, Kgs. Lyngby (DK)

( * ) Notice: Subject to any disclaimer, the term of this patent is extended or adjusted under 35 U.S.C. 154(b) by 0 days.

(21) Appl. No.: 17/261,235

(22) PCT Filed: Jul. 11, 2019

(86) PCT No.: PCT/EP2019/068678
§ 371 (c)(1),
(2) Date: Jan. 19, 2021

(87) PCT Pub. No.: WO2020/035231
PCT Pub. Date: Feb. 20, 2020

(65) Prior Publication Data
US 2021/0269380 A1   Sep. 2, 2021

(30) Foreign Application Priority Data

Aug. 17, 2018 (DK) .......................... PA 2018 00475

(51) Int. Cl.
*C07C 29/152* (2006.01)
*C07C 29/151* (2006.01)

(52) U.S. Cl.
CPC ........ *C07C 29/152* (2013.01); *C07C 29/1518* (2013.01)

(58) Field of Classification Search
CPC . C07C 29/152; C07C 29/151; C07C 29/1518; C07C 31/04
See application file for complete search history.

(56) References Cited

U.S. PATENT DOCUMENTS

| | | | |
|---|---|---|---|
| 8,536,235 | B2 | 9/2013 | Fitzpatrick |
| 2011/0065966 | A1 | 3/2011 | Mueeller et al. |

FOREIGN PATENT DOCUMENTS

| | | | | |
|---|---|---|---|---|
| CN | 107382665 A | 11/2017 | | |
| WO | 2006018610 A1 | 2/2006 | | |
| WO | WO-2016150858 A1 * | 9/2016 | .............. | B01J 8/067 |
| WO | 2017186538 A1 | 11/2017 | | |
| WO | 2019008317 A1 | 1/2019 | | |

OTHER PUBLICATIONS

International Search Report (PCT/ISA/210) with translation and Written Opinion (PCT/ISA/237) dated Oct. 2, 2019, by the European Patent Office as the International Searching Authority for International Application No. PCT/EP2019/068678.

* cited by examiner

*Primary Examiner* — Jafar F Parsa
(74) *Attorney, Agent, or Firm* — Buchanan Ingersoll & Rooney P.C.

(57) ABSTRACT

A method for producing methanol comprises the steps of passing a feed stream of methanol synthesis pas through a main methanol reactor containing a methanol synthesis catalyst, to form a mixed gas containing methanol, cooling the mixed gas containing methanol, separating methanol from the mixed pas and heating the mixed gas. The stream of heated mixed gas is passed through an additional methanol reactor containing a methanol synthesis catalyst, and the effluent from the additional methanol reactor is mixed with the feed stream of methanol synthesis gas and passed through the main methanol reactor.

12 Claims, No Drawings

METHOD FOR PRODUCING METHANOL IN A REACTOR WITH BYPASS

The present invention relates to a method for producing methanol in a reactor provided with a bypass in the form of an additional methanol reactor.

In a traditional methanol loop, feed gas is compressed and mixed with recycled unreacted gas before being sent to the methanol reactor, in which methanol is produced from synthesis gas (syngas) via equilibrium reactions proceeding at elevated temperature under elevated pressure. The synthesis reactions are:

$$CO+H_2O <-> CH_3OH+heat \quad (1)$$

$$CO_2+3H_2 <-> CH_3OH+H_2O+heat \quad (2)$$

$$CO+H_2O <-> CO_2+H_2+heat \quad (3)$$

Because the reactions are exothermal, the methanol reactor has to be equipped with a lot of cooling tubes to control the temperature.

In order to reduce the size of the traditional methanol reactor (or to boost the production), it is advantageous to install a catalyst layer in an additional reactor upstream. the traditional reactor. This additional reactor may be a less complicated or less cooled (alternatively adiabatic) reactor. However, if the new additional reactor is an adiabatic reactor (alternatively less cooled), the temperature profile will vary with capacity, gas composition and catalyst activity, and there is a risk of too high temperatures at the outlet of the catalyst bed. High temperatures in the catalyst bed will lead to an increased formation of by-products and to catalyst sintering.

U.S. Pat. No. 8,536,235 discloses a process for the synthesis of methanal comprising (a) passing a synthesis as mixture of a loop gas and a make-up gas through a first synthesis reactor cooled by boiling water under pressure and containing a methanol synthesis catalyst, to form a mixed gas containing methanol, (b) cooling said maxed gas, (c) passing said mixed gas through a second synthesis reactor containing a methanol synthesis catalyst, where further methanol is synthesized to form a product gas stream, (d) cooling said product gas stream to condense methanol, and (e) recovering the methanol and returning unreacted gas as the loop gas to the first synthesis reactor. The mixed gas containing methanol from the first synthesis reactor is cooled in heat exchange with either the loop gas or the make-up gas.

CN 107382665 A discloses a technology for synthesizing methanol, comprising generating methanol from a synthesis gas containing fresh gas through a first reactor, exchanging the heat of the mixed as containing the synthesis gas and methanol steam with the heat of the synthesis gas containing fresh gas to be fed into the first reactor and then generating methanol through a second reactor, cooling the synthesis gas of higher methanol concentration after the reaction, and then guiding it into a methanol separator and separating methanol, mixing the synthesis gas after separating methanol with fresh gas, thereby acquiring the synthesis gas containing fresh gas, guiding the synthesis gas containing fresh gas into the first reactor again, utilizing a valve A to directly guide a part of fresh gas into the second reactor and controlling the hot-spot temperature of a catalyst bed of the second reactor to around 250° C., keeping a part of synthesis gas containing fresh gas free from heat exchange and directly introducing it into the first reactor by a valve B and controlling the gas inlet temperature of the second reactor at 200-240° C. This way, the use ratio of the catalyst is increased and the quality of the methanol product is improved.

In US 2011/0065966, the synthesis gas containing hydrogen and carbon oxides for the production of methanol is passed through a first, preferably water-cooled reactor, in which a part of the carbon oxides is catalytically converted to methanol. The resulting mixture containing synthesis gas and methanol vapour is fed to a second, preferably gas-cooled reactor, in which a further part of the carbon oxides is converted to methanol. To achieve a maximum methanol yield, even with an aged catalyst, a partial stream of the synthesis gas is guided past the first reactor and introduced directly into the second reactor.

To increase the capacity of a cooling medium reactor, the catalyst in some cases be loaded not only into the reaction tubes, but also further up above the upper tube sheet wherein the reaction tubes are mounted. As regards exothermal reactions, this wilt Increase the reaction gas temperature even before the reactant reaches the reaction tubes which are in thermal contact with the cooling medium. Thus there is a risk that the temperature of the tube sheet gets too high, with the consequent risk of damage to the tube sheet or damage to the top of the reaction tubes and the upper tube sheet. This problem is solved by Applicant's WO 2017/186538, which discloses a cooling medium reactor for an exothermal reaction. The reactor comprises reaction tube inserts to provide for an adiabatic catalyst layer on top of the upper tube sheet inserts arranged on top of the upper tube sheet and a guide means of the inserts which thermally insulates the upper tube sheet from the exothermal reaction within the inserts.

The object of the present invention is to add an extra reactor and to arrange a feed gas bypass around the first (or more) reactor(s) in order to control the temperature at the reactor outlet. The feed gas that is bypassed has a lower temperature, and it is mixed with the hot gas at the outlet of the reactor to control the temperature at the desired level. The gas bypass is taken from the feed gas, allowing the full flow of recycled gas to pass through the first reactor and reducing the amount of fresh feed gas to the adiabatic (or less cooled) reactor as shown in the appended figure.

So the present invention relates to a method for producing methanol, comprising the steps of
(a) passing a feed stream of methanol synthesis gas through a main methanol reactor containing a methanol synthesis catalyst, to form a mixed gas containing methanol,
(b) cooling the mixed gas containing methanol,
(c) separating methanol from the mixed gas and
(d) heating the mixed gas,
wherein
the stream of heated mixed gas from step (d) is passed through an additional methanol reactor containing a methanol synthesis catalyst, and
the effluent from the additional methanol reactor is mixed with the feed stream of methanol synthesis gas and passed through the main methanol reactor.

To reduce the size of the boiling water reactor (BWR) the methanol loop (or alternatively boost the production of an existing BWR), an adiabatic catalyst layer can be placed. on top of the tube sheet. For large units, it could be an advantage to place the adiabatic bed in a separate reactor. The major difference between this idea and the adiabatic top layer (catalyst inserts) described in. WO 2017/186538 is the ability to control outside the cooled reactor, which makes it possible to operate the loop in a different way. If the catalyst bed is placed in a separate reactor, then it is possible to add an extra control to limit the temperature in low load or transient cases.

As the fresh gas to the new reactor is reduced, the gas at the inlet of the additional reactor is less reactive, which leads to a lower peak temperature in the catalyst bed and a lower by-product formation.

The idea of utilizing an additional reactor upstream the existing methanol reactor and controlling the outlet temperature (the existing reactor inlet temperature) by gas bypass is illustrated in the appended figure:

The stream of methanol synthesis feed gas f is split into two streams, one of which is sent to the main methanol reactor A via a throttle valve while the other is sent to the additional methanol reactor B after passing a feed/effluent heat exchanger Hex.

Thus, the main methanol reactor A is fed with a mixture of fresh methanol synthesis feed gas f and the effluent e2 from the additional methanol reactor B.

The effluent e1 from the main methanol reactor A is cooled in a loop air cooler lac and a loop water cooler lwc and then fed to a separator S, where liquid methanol product (MeOH) is separated from the gas phase, the latter being mixed with fresh feed gas and passed to the additional methanol reactor B.

The invention claimed is:

1. A method for producing methanol, comprising the steps of
   (a) passing a feed stream of methanol synthesis gas through a main methanol reactor containing a methanol synthesis catalyst, to form a mixed gas containing methanol,
   (b) cooling the mixed gas containing methanol,
   (c) separating methanol from the mixed gas and
   (d) heating the mixed gas, wherein
   the stream of heated mixed gas from step (d) is passed through an additional methanol reactor containing a methanol synthesis catalyst,
   the effluent from the additional methanol reactor is mixed with the feed stream of methanol synthesis gas and passed through the main methanol reactor,
      either the main methanol reactor or the additional methanol reactor comprises a tube sheet.

2. The method according to claim 1, wherein the main methanol reactor is a boiling water reactor (BWR).

3. The method according to claim 2, wherein an adiabatic catalyst layer is placed on top of the tube sheet.

4. The method according to claim 3, wherein the main methanol reactor comprises the tube sheet.

5. The method according to claim 3, wherein the additional methanol reactor comprises the tube sheet.

6. The method according to claim 1, wherein each of the main methanol reactor and the additional methanol reactor comprises a tube sheet.

7. The method according to claim 3, wherein each of the main methanol reactor and the additional methanol reactor comprises a tube sheet.

8. The method according to claim 1, wherein the feed stream of methanol synthesis gas is split into a first stream and a second stream before reaching the main methanol reactor.

9. The method according to claim 8, wherein the first stream is sent to the main methanol reactor via a throttle valve, and the second stream is sent to the additional methanol reactor after passing a feed/effluent heat exchanger.

10. The method according to claim 1, wherein effluent from the main methanol reactor is cooled in a loop air cooler and a loop water cooler before being fed to a separator in which liquid methanol product is separated from the gas phase.

11. The method according to claim 10, wherein, the gas phase leaving the separator is mixed with fresh feed gas and then passed to the additional methanol reactor.

12. The method according to claim 1, wherein the feed stream of methanol synthesis gas is split into a first stream and a second stream before reaching the main methanol reactor,
   wherein the first stream is sent to the main methanol reactor via a throttle valve, and the second stream is sent to the additional methanol reactor after passing a feed/effluent heat exchanger,
   wherein effluent from the main methanol reactor is cooled in a loop air cooler and a loop water cooler before being fed to a separator in which liquid methanol product is separated from the gas phase, and
   wherein, the gas phase leaving the separator is mixed with fresh feed gas and then passed to the additional methanol reactor.

* * * * *